US010189866B2

(12) United States Patent
Haruna et al.

(10) Patent No.: US 10,189,866 B2
(45) Date of Patent: Jan. 29, 2019

(54) LITHIUM SECONDARY BATTERY, ELECTROLYTE SOLUTION FOR LITHIUM SECONDARY BATTERY, AND ADDITIVE FOR ELECTROLYTE SOLUTION THEREFOR

(71) Applicant: HITACHI, LTD., Tokyo (JP)

(72) Inventors: Hiroshi Haruna, Tokyo (JP); Shin Takahashi, Tokyo (JP); Toshio Abe, Tokyo (JP); Yasutaka Tanaka, Shizuoka (JP)

(73) Assignee: HITACHI, LTD., Tokyo (JP)

( * ) Notice: Subject to any disclaimer, the term of this patent is extended or adjusted under 35 U.S.C. 154(b) by 45 days.

(21) Appl. No.: 15/046,669

(22) Filed: Feb. 18, 2016

(65) Prior Publication Data
US 2016/0237098 A1    Aug. 18, 2016

(30) Foreign Application Priority Data
Feb. 18, 2015    (JP) ................................. 2015-029190

(51) Int. Cl.
*H01M 10/0525*    (2010.01)
*C07F 5/05*    (2006.01)
(Continued)

(52) U.S. Cl.
CPC ........... *C07F 5/05* (2013.01); *H01M 10/0525* (2013.01); *H01M 10/0567* (2013.01); *H01M 10/0568* (2013.01); *Y02T 10/7011* (2013.01)

(58) Field of Classification Search
None
See application file for complete search history.

(56) References Cited

U.S. PATENT DOCUMENTS 5,891,592 A      4/1999  Mao et al.
2006/0281012 A1* 12/2006  Ugawa ................ H01M 10/052
                                                                 429/330
(Continued)

FOREIGN PATENT DOCUMENTS

EP    0856901 A1    8/1998
EP    2728660 A1    5/2014
(Continued)

OTHER PUBLICATIONS

Zhang, J., et al., "Influences of Additives on the Formation of a Solid Electrolyte Interphase on MnO Electrode Studied by Atomic Force Microscopy and Force Spectroscopy," Journal of Physical Chemistry C, vol. 118, No. 36, Sep. 11, 2014 (Sep. 11, 2014), pp. 20756-20762—Reference listed in Extended European Search Report.
(Continued)

*Primary Examiner* — Wyatt P McConnell
(74) *Attorney, Agent, or Firm* — Volpe and Koenig, P.C.

(57) ABSTRACT

Provided are a lithium secondary battery having improved initial capacity and excellent cycle property, an electrolyte solution for the lithium secondary battery, and an additive for the electrolyte solution for the lithium secondary battery. The lithium secondary battery includes positive and negative electrodes both having a lithium-ion intercalation/de-intercalation ability, and a non-aqueous electrolyte solution contacted with the positive and negative electrodes. The non-aqueous electrolyte solution contains lithium hexafluorophosphate and a boroxine compound represented by $(RO)_3(BO)_3$ liquefying at 25° C. R(s) each independently represent an organic group of a linear chain alkyl group having 3 or more carbon atoms. Herein, the chain alkyl group may have a branch, and when the branch is included, the number of carbon atoms of the chain alkyl group constructing a linear portion thereof is 3 or more.

7 Claims, 2 Drawing Sheets

(51) Int. Cl.
  *H01M 10/0567* (2010.01)
  *H01M 10/0568* (2010.01)

(56) References Cited

U.S. PATENT DOCUMENTS

| | | | |
|---|---|---|---|
| 2007/0077496 A1 | 4/2007 | Scott et al. | |
| 2007/0295956 A1* | 12/2007 | Haitko | C08G 59/3245 257/40 |
| 2011/0008680 A1* | 1/2011 | Muldoon | C07C 307/02 429/325 |
| 2015/0263386 A1* | 9/2015 | Markevich | H01M 4/386 429/327 |

FOREIGN PATENT DOCUMENTS

| | | |
|---|---|---|
| EP | 2840639 A1 | 2/2015 |
| JP | 10223258 | 8/1998 |
| JP | 2003303617 A | 10/2003 |
| JP | 2007165108 A | 6/2007 |
| JP | 2007273260 A | 10/2007 |
| JP | 2014-222653 A | 11/2014 |
| WO | 2012/133556 A1 | 10/2012 |
| WO | 2014/067891 A1 | 5/2014 |

OTHER PUBLICATIONS

Horino, T., et al., "High Voltage Stability of Interfacial Reaction at the LiMn2O4 Thin-Film Electrodes/Liquid Electrolytes with Boroxine Compounds," Journal of the Electrochemcial Society, Electrochemical Society, vol. 157, No. 5, Jan. 1, 2010, (Jan. 1, 2010), pp. A677-A681—Reference listed in Extended European Search Report.
Sigma-Aldrich "Sigma-Aldrich Safety Data Sheet: Aldrich-S343064", pp. 1-6, XP055339132, [retrieved on Jan. 26, 2017].
Communication dated Feb. 1, 2017 in the EP Application No. 16156203.8.
Mengqing Xu "Electrolytes for Lithium-Ion Batteries with High-Voltage Cathodes": Lithium Batteries, Advanced Technologies and Applications. John Wiley & Sons, Inc. 2013, 1st edition, pp. 71-87.
Korean Office Action dated May 23, 2017 in the Korean Application No. 10-2016-0016983.
Office Action in counterpart KR Application No. 10-2016-0016983 dated Nov. 10, 2017.
Office Action in counterpart JP Application No. 2015-029190 dated Dec. 5, 2017.

* cited by examiner

LITHIUM SECONDARY BATTERY, ELECTROLYTE SOLUTION FOR LITHIUM SECONDARY BATTERY, AND ADDITIVE FOR ELECTROLYTE SOLUTION THEREFOR

BACKGROUND OF THE INVENTION

1. Field of the Invention

The present invention relates to a lithium secondary battery, an electrolyte solution for the lithium secondary battery, and an additive for the electrolyte solution for the lithium secondary battery.

2. Related Art

Reduction in size and increase in energy density (or capacity) of a power source used in a mobile communication device such as a cellular phone or a portable personal computer in recent years have been demanded more and more. Further, practical use of a power source in a ship, a hybrid train, a hybrid car and an electric vehicle using electric power as a part of driving power has been under progress. Moreover, with a viewpoint of environmental protection, development has been progressed not only for the storage of midnight power but also for a power source used for power storage in combination with solar cells and wind power generation or a smart grid. Under this circumstance, a lithium secondary battery has attracted much attention.

However, repeated charge/discharge processes deteriorate the charge/discharge efficiency of a lithium secondary battery, and increase internal resistance thereof. Thus, a lithium secondary battery with less aging deterioration of the battery performance has been demanded.

Here, a technology for satisfying the above demand is known as described in International Patent Publication No. WO2012/133556. This patent document discloses use of an electrolyte solution for a lithium secondary battery having a repeated charge ability at a high voltage. Specifically, described is an electrolyte solution for a lithium secondary battery including a mixture of at least one solvent selected from a carbonate ester and a borate ester, LiBF$_4$, and a predetermined boroxine compound.

Further, the above patent document describes that the lithium secondary battery using the electrolyte solution described therein has a repeated charge ability at a high voltage. However, the patent document does not describe improvement of initial capacity and cycle property of the lithium secondary battery using the electrolyte solution. Therefore, increase in the capacity of a lithium secondary battery as well as suppression of aging deterioration thereof have not been sufficiently achieved in the prior art.

SUMMARY OF THE INVENTION

In view of the drawbacks described above, the present invention has been developed. Therefore, an object of the present invention is to provide a lithium secondary battery having improved initial capacity as well as excellent cycle property, an electrolyte solution for the lithium secondary battery, and an additive for the electrolyte solution for the lithium secondary battery.

The present inventors have earnestly investigated to solve the drawbacks and reached the finding that those drawbacks are solved when a predetermined boroxine compound liquefying at 25° C. is incorporated in an electrolyte solution, whereby the present invention is accomplished.

According to the present invention, provided are a lithium secondary battery having improved initial capacity as well as excellent cycle property, an electrolyte solution for the lithium secondary battery, and an additive for the electrolyte solution for the lithium secondary battery.

DETAILED DESCRIPTION OF THE PRESENT INVENTION

Hereinafter, embodiments for carrying out the present invention will be described in detail referring to the attached drawings.

Figure 1:
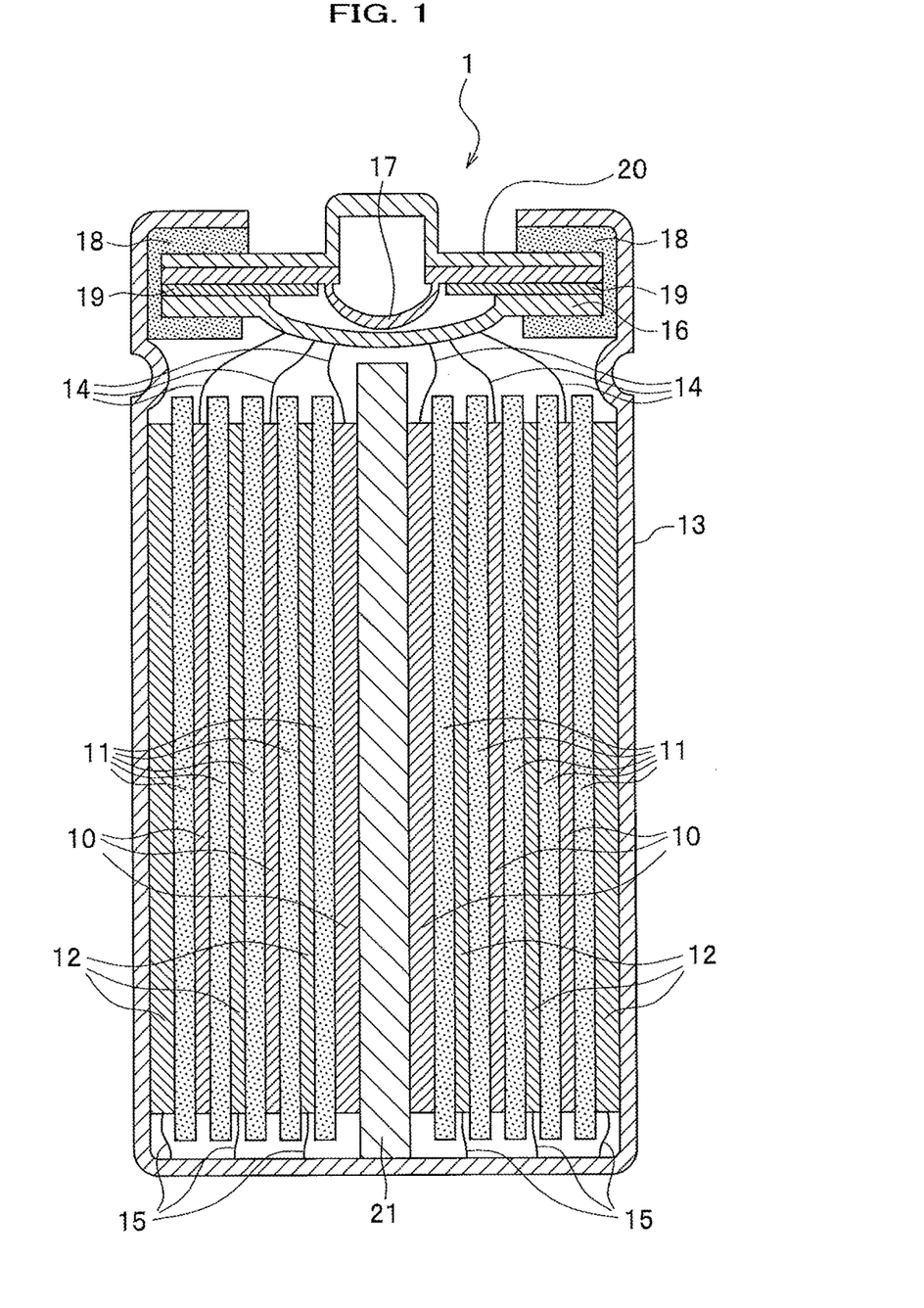
FIG. 1 is a schematic diagram showing an internal structure of a lithium secondary battery in an embodiment of the present invention.

FIG. 1 is a schematic diagram showing an internal structure of a lithium secondary battery in an embodiment of the present invention. As shown in FIG. 1, a lithium secondary battery 1 is configured including at least a positive electrode 10 and a negative electrode 12 both having a lithium-ion intercalation/de-intercalation ability. The positive electrode 10 and negative electrode 12 are housed in a battery container 13. Further, an electrolyte solution (e.g., also referring to "an electrolyte solution for a lithium secondary battery" or "a non-aqueous electrolyte solution") is filled inside the battery container 13. Herein, lithium-ions transfer among the electrolyte solution, the positive electrode 10 and the negative electrode 12. The lithium secondary battery 1 is charged/discharged associated with the ionic transfer.

<Electrolyte Solution>

An electrolyte solution filled in the battery container 13 contains a boroxine compound represented by the following Formula (1), a non-aqueous solvent and lithium hexafluorophosphate (LiPF$_6$) serving as an electrolyte. The boroxine compound represented by Formula (1) liquefies at 25° C. Hereinafter, the boroxine compound represented by Formula (1) may be referred to a "boroxine compound (1)". Similarly, the chemical structure represented by Formula (1) may be abbreviated to "(RO)$_3$(BO)$_3$".

Formula (1)

where R(s) each independently represent an organic group of a linear chain alkyl group having 3 or more carbon atoms. Herein, the linear chain alkyl group may further include a branch, and when including the branch, the number of the carbon atoms constructing a linear portion of the chain alkyl group is 3 or more.

Use of the boroxine compound (1) liquefying at 25° C. allows solubility thereof in a non-aqueous solvent to be increased, thereby demonstrating the maximum advantage of the boroxine compound (1). Further, a device for solving the boroxine compound (1) may be simplified due to the easy solubilization of the compound (1).

The boroxine compound (1) is prepared by replacing the three hydrogen atoms in boroxine ($B_3H_3O_3$) with alkoxy groups (i.e., —OR). The three R groups thus included in the boroxine compound (1) may be the same. Alternatively, a part of the R groups may be different from the remaining R group (s), or all of the R groups may be different each other.

In the boroxine compound (1), R(s) each represent independently an organic group of a linear chain alkyl group having 3 or more carbon atoms. Here, "a linear chain alkyl group having 3 or more carbon atoms" means that among the linear alkyl groups of the organic group constructing R(s), the number of the carbon atoms constructing the longest chain alkyl group is 3 or more. Additionally, the chain alkyl group may further include a branch, and in such a case the number of the carbon atoms constructing the linear portion is 3 or more. This structural profile allows the bulkiness of the boroxine compound to be made higher than that of boroxine due to 3-D structural change, leading to identification of the boroxine compound (1) liquefying at 25° C.

Note the organic group constructing R(s) may be preferably a linear chain alkyl group having 3 or more carbon atoms, and optionally further include a branch. Since the organic group is an alkyl group, a boroxine compound (1) may be easily prepared by using, for example, the Grignard reaction. Here, for convenience in the following descriptions, R(s) represent "a linear chain alkyl group having 3 or more carbon atoms, and optionally further including a branch" serving as a preferable example.

Further, the number of the carbon atoms contained in the organic group constructing R(s) is not specifically limited. However, in view of easy preparation, preferably the upper limit of the number of the carbon atoms may be 6 or less. Moreover, the alkyl group may be a saturated alkyl group. R(s) may include an optional element (e.g., halogen, nitrogen, and sulfur or the like).

Specific examples of the chain alkyl group include, but are not particularly limited by the following examples:

a linear chain alkyl group represented by $R=C_aH_b$ (where C represents a carbon atom, H represents a hydrogen atom, a is an integer of 3 or more, and b is the number satisfying the equation of b=2a+1), specifically including a linear hydrocarbon group such as a propyl group, a butyl group, a hexyl group, a heptyl group, an octyl group, a nonyl group, a decyl group or the like;

a linear chain alkyl group further having a branch represented by $R=C_cH_d$ (where C represents a carbon atom, H represents a hydrogen atom, c is an integer of 4 or more, and d is the number satisfying the equation of d=2a+1), specifically including a 1-methyl-propyl group, a 1-ethyl propyl group, a 2-methyl-propyl group, a 1-methyl butyl group, 1-ethyl butyl group, 2-methyl butyl group, a 2-ethyl butyl group, a 3-methyl butyl group, a 1-methyl pentyl group, a 1-ethyl pentyl group, a 1-propyl pentyl group, a 2-methyl pentyl group, a 2-ethyl pentyl group, a 2-propyl pentyl group, a 3-methyl pentyl group, a 3-ethyl pentyl group, a 4-methyl pentyl group, a 1-methyl hexyl group, a 1-ethyl hexyl group, a 1-propyl hexyl group, a 1-buthyl hexyl group, a 1-penthyl hexyl group, a 2-methyl hexyl group, a 2-ethyl hexyl group, a 2-propyl hexyl group, a 2-buthyl hexyl group, a 3-methyl hexyl group, a 3-ethyl hexyl group, a 3-propyl hexyl group, a 4-methyl hexyl group, a 4-ethyl hexyl group, and a 5-methyl hexyl group or the like.

Next, a reason why the above defined boroxine compound (1) liquefies at 25° C., thereby achieving the advantageous effects of the present invention will be described more specifically.

A tricoordinate compound in which three ligands coordinate a boron atom (e.g., B—$H_3$ in which three hydrogen atoms coordinate one boron atom) generally has a trigonal planar structure. Therefore, it is assumed that a cyclic structure represented by $(B-O)_3$ (i.e., a skeleton geometry of the boroxine ring) has a planar structure. In other words, in a boroxine compound having such a skeleton geometry, the vacant p-orbital of the boron atom and the lone pair of the oxygen atom forma π-orbital, so that the boroxine compound is isoelectronic to benzene having aromaticity. Thereby, a boroxine compound may have aromaticity. Further, a single bond of the boron atom in a boroxine compound is mostly s-orbital character, which may suppress the influence of the substituent on the size of the boroxine ring (i.e., skeleton structure of $(B-O)_3$). As a result, sizes of different boroxine rings may be almost the same without depending on the size of the substituent.

The boroxine compound (1) is represented by $(B-O)_3$ in which the substituent (i.e., alkoxy group) represented by "—OR" is bonded to each boron atom. Therefore, the alkoxy group may not have a large influence on the electronic state of the skeleton geometry of the boroxine ring. In particular, an electron donating effect of the oxygen atom included in the alkoxy group may be large on the boroxine ring having aromaticity, while electron withdrawing and induction effects of the different kinds of R may be almost the same. Therefore, when R has the above structure, the same effect may be achieved on the respective boroxine compounds (1).

Here, the boroxine compound (1) is a substance liquefying at 25° C. A boroxine ring of the boroxine compound (1) is assumed to have a planar structure as described hereinbefore. However, three Rs included in the boroxine compound (1) are assumed to respectively have high bulkiness, which is likely to impair the planar structure of the boroxine ring. Accordingly, this structural influence may make the boroxine compound (1) liquefy at 25° C. Thus, use of the boroxine compound liquefying at 25° C. facilitates the boroxine compound (1) to be miscible in an electrolyte solution, thereby more easily exerting an advantage effect of the boroxine compound (1).

The boroxine compound (1) may be produced, for example, via a reaction between an alkyl magnesium chloride serving as a Grignard reagent and trimethyl borate. An alkyl group of the alkyl magnesium chloride may be suitably selected corresponding to R of the boroxine compound (1). That is, a variety of boroxine compounds (1) including a variety of alkyl groups of Rs may be produced by selecting corresponded alkyl magnesium chloride(s). Further, a boroxine compound (1) having different alkyl groups in a molecule (i.e., chemical formula of $(OR_1)(OR_2)(OR_3)(BO)_3$ (where $R_1$-$R_3$ represent organic groups different from each other)) may be obtained, for example, by using a plurality types of alkyl magnesium chlorides and changing the number of mols to be added into the reaction.

Moreover, the boroxine compound (1) may be also produced, for example, via a cyclization reaction between a trialkyl borate: $B(OR)_3$ and $B_2O_3$. In this reaction, a variety of boroxine compounds (1) bonded with a variety of organic groups of Rs may be produced by, for example, selecting $B(OR)_3$. Furthermore, a boroxine compound (1) having different alkyl groups in a molecule (i.e., chemical formula of $(OR_1)(OR_2)(OR_3)(BO)_3$ (where $R_1$-$R_3$ represent organic groups different from each other)) may be obtained, for example, by allowing a plurality types of B(OR)$_3$ having different alkyl groups Rs (e.g., a mixture of B(OR$_1$), B(OR$_2$) and B(OR$_3$) each included at a predetermined mol ratio) to react with boric anhydride B$_2$O$_3$.

In the above reactions, especially in the cyclization reaction, the targeted boroxine compound (1) may be obtained by allowing B(OC$_4$H$_9$)$_3$ to react with B$_2$O$_3$ at the equimolar amounts. Accordingly, formation of products such as unreacted reactants and by-products, etc. other than the boroxine compound (1) may be suppressed. In this preparation method, if the targeted boroxine compound (1) is added into the electrolyte solution for the lithium secondary battery, to be used as an additive for the electrolyte solution, this procedure prevents compounds other than the boroxine compound (1) from being included in the electrolyte solution. Therefore, this preparation method is advantageous to prepare an additive with a high grade of purity used for an electrolyte solution of a lithium secondary battery.

As mentioned above, the electrolyte solution contains lithium hexafluorophosphate (i.e., formed by ionic binding between Li$^+$ and PF6$^-$). In the electrolyte solution of the present invention, the boroxine compound as mentioned above coexists with lithium hexafluorophosphate. This coexistence allows both the compounds to react with each other, thereby giving a boroxine compound (1) in which at least one of the boron atoms (i.e., usually in a trivalent form) takes a tetravalent form. This type of reaction may enhance a dissociation degree of lithium-ions, resulting in further enhancement of the battery capacity.

A possible reaction mechanism for formation of the above product may be explained as follows. In a boroxine compound represented by (RO)$_3$ (BO)$_3$, electron density of the boron atoms constructing the (B—O)$_3$ ring having aromaticity is lowered. As a result, such a boron atom forms a complex with an electron rich PF6$^-$ anion in the electrolyte solution. Through the complex formation reaction, the valence of the boron atom changes from a trivalent to a tetravalent form. On the other hand, in the electrolyte solution, Li$^+$ of the electrolyte interacts with the PF$_6^-$ anion of the electrolyte. However, if the PF$_6^-$ anion interacts with the boron atom of the (B—O)$_3$ ring as described above, the equilibrium reaction shown in the following chemical reaction equation (2) advances to the right direction. This change in the equilibrium facilitates the dissociation of Li$^+$, thereby to increase the amount of Li$^+$ contributing to the cell reaction in the electrolyte solution. Eventually, the increased amount of Li$^+$ makes the battery capacity highly increased.

Chemical Reaction Equation (2)

The equilibrium reaction starts particularly at the time when the boroxine compound (1) has coexisted with lithium hexafluorophosphate in the electrolyte solution. Thus, the dissociation of Li$^+$ starts at the time when the boroxine compound (1) and lithium hexafluorophosphate have been dissolved in the electrolyte solution. The dissociation of Li$^+$ increases the initial capacity of the lithium secondary battery 1 assembled by incorporating the above electrolyte solution. Further, the above equilibrium reaction proceeds while the lithium secondary battery 1 is charged/discharged. That is, the dissociation of Li$^+$ is appropriately facilitated corresponding to the advancement of the equilibrium reaction in progress during the charge/discharge processes. The Li$^+$ dissociation thus facilitated prevents deterioration of the cycle property of the lithium secondary battery 1 caused via deterioration of active materials. Accordingly, the cycle property of the lithium secondary battery 1 is improved.

Here, the equilibrium reaction can be monitored by $^{11}$B-NMR measurement based on a chemical shift of the boron atom. Note the chemical shift of the boron atom reflects the electron density of the measured boron atom. Therefore, $^{11}$B-NMR measurement was performed by the following procedure in order to check the occurrence of the equilibrium reaction in the electrolyte solution containing the boroxine compound (1) and lithium hexafluorophosphate.

As a boroxine compound (1), (O—CH$_2$CH$_2$CH$_2$CH$_3$)$_3$ (BO)$_3$ was used. This is a compound represented by Formula (1) in which R is a linear alkyl group having 4 carbon atoms (i.e., butyl group). Then, as an electrolyte solution, the following solution was prepared by dissolving the boroxine compound (1) and lithium hexafluorophosphate into a mixed solution of non-aqueous solvents of ethylene carbonate (EC) and ethyl methyl carbonate (EMC) (where EC:EMC=1:3 (at volume ratio)) so that each mass molar concentration of the respective reagents became 1.0 mol/kg. Hereinafter, the electrolyte solution may be called "a mixed electrolyte solution". In addition, an electrolyte solution serving as a comparison reference (hereinafter, this electrolyte solution may be called "a single electrolyte solution") was obtained by the same method as for the mixed electrolyte solution except that the single electrolyte solution included no lithium hexafluorophosphate.

Figure 2:
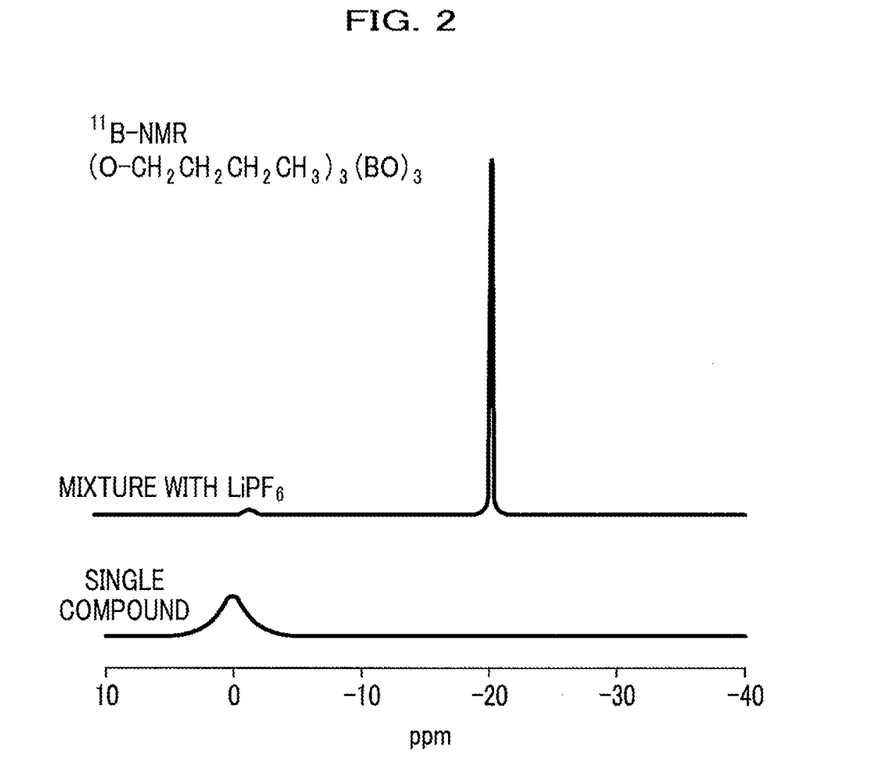
FIG. 2 is a diagram showing $^{11}$B-NMR spectra of the boroxine compound (1).

$^{11}$B-NMR spectra of both electrolyte solutions were measured respectively. FIG. 2 shows the respective $^{11}$B-NMR spectra.

FIG. 2 is a diagram showing $^{11}$B-NMR spectra of the boroxine compound (1). In FIG. 2, the upper side one shows a $^{11}$B-NMR spectrum of an electrolyte solution containing both the boroxine compound (1) and lithium hexafluorophosphate. The lower side one shows a $^{11}$B-NMR spectrum of an electrolyte solution containing the boroxine compound (1) alone without lithium hexafluorophosphate.

In the lower side spectrum (i.e., single electrolyte solution), a single peak (i.e., one component) alone was observed near at 0 ppm. On the contrary, in the upper side spectrum (i.e., mixed electrolyte solution of the boroxine compound (1) and lithium hexafluorophosphate), a peak (i.e., another component) was additionally observed shifted at about 20 ppm high magnetic field side from the peak near at 0 ppm. The results demonstrate that the valence number of the boron atom constructing the boroxine compound (1) changes in the electrolyte solution including the boroxine compound (1) and lithium hexafluorophosphate.

Further, although it is not illustrated, a $^{11}$B-NMR spectrum of boric acid having the known valence number (i.e., trivalent) was measured. Then, the chemical shift of the $^{11}$B-NMR spectrum of boric acid serving as an external standard was compared to the chemical shift of the $^{11}$B-NMR spectrum in FIG. 2. Accordingly, the chemical shift of the single electrolyte solution in FIG. 2 was observed at substantially the same position as that of boric acid.

On the other hand, in the mixed electrolyte solution, two kinds of chemical shifts were observed at substantially the same position as that of boric acid, and additionally at the position shifted about 20 ppm high magnetic field side from the peak of boric acid. As mentioned above, it was confirmed that a trivalent compound and a compound with the larger valence number (e.g., tetravalent) were mixed in the mixed electrolyte solution.

Note 2-D NMR or $^1$H-NMR may be used in combination to check such a structural change in more detail.

Further, research of the present inventors reveals that when lithium tetrafluoborate (LiBF$_4$) is used instead of lithium hexafluorophosphate in the mixed electrolyte solution originally containing the boroxine compound (1) and lithium hexafluorophosphate, the above phenomenon (i.e., change in the valence number of the boron atom in the electrolyte solution) is not confirmed. Here, this confirmation research was performed by $^{11}$B-NMR and $^{1}$H-NMR.

The research of the present inventors suggests a reason why such a difference occurs in the NMR measurement as the followings. An anion "$BF_4^-$" composing lithium tetrafluoborate consists of one boron atom and 4 fluorine atoms. Due to a small ionic radius of the boron atom, whole of the surface area of "$BF_4^-$" including those atoms becomes relatively small. This relatively small surface area increases the negative charge on the surface of the anion, allowing "$BF_4^-$" to form a relatively strong bond with a lithium-ion positively charged. Thereby, dissociation of the lithium-ion forming the relatively strong bond with "$BF_4^-$" becomes more difficult in the electrolyte solution. As a result, it is assumed that lithium tetrafluoborate ($LiBF_4$) seldom reacts with the boroxine compound (1).

On the other hand, an anion "$PF_6^-$" composing lithium hexafluorophosphate consists of one phosphor atom and 6 fluorine atoms. The radius of the phosphor atom is larger than that of the fluorine atom. The total number of atoms (i.e., 7) composing "$PF_6^-$" formed of those atoms is more than the total number of atoms (i.e., 5) composing "$BF_4^-$". Due to this, whole of the surface area of "$PF_6^-$" becomes relatively large compared to that of "$BF_4^-$". This relatively large surface area decreases the negative charge on the surface of "$PF_6^-$" to be relatively small, having "$PF_6^-$" form a relatively weak bond with a lithium-ion positively charged. Thereby, the lithium-ion forming a relatively weak ionic bond with "$PF_6^-$" easily dissociates in the electrolyte solution. As a result, it is assumed that the lithium-ion dissociating more easily in the electrolyte solution more easily coordinates with the boron atom having larger electron density in the boroxine compound (1). The easier coordination can vary the valence number of the boron atom as mentioned hereinbefore.

As mentioned above, the interaction between the boron atom of the boroxine compound (1) and the electrolyte varies corresponding to a counter anion of the electrolyte. Further, the interaction is thermodynamic. Therefore, the interaction can be clearly determined by measuring a target sample under temperature-variable conditions like at low to high temperatures.

The amounts of the boroxine compound (1) and lithium hexafluorophosphate contained in the electrolyte solution are not limited specifically. However, for facilitating the interaction therebetween, preferably the content of the boroxine compound (1) included in the electrolyte solution is set at 0.1 to 2 mass % or less, represented as a concentration in the electrolyte solution (i.e., generally with respect to the total content of lithium hexafluorophosphate and the boroxine compound (1)). More preferably, the content of the boroxine compound (1) is set at 0.3 to 0.8 mass %. Setting-up those ranges enables the solubility of the boroxine compound (1) and the advantageous effect thus achieved to be in particularly excellent balance.

Moreover, the concentration of lithium hexafluorophosphate included in the electrolyte solution is not specifically limited. However, preferably the concentration of all the electrolytes (e.g., lithium tetrafluoroborate) including lithium hexafluorophosphate is set in 0.6 to 1.5 mol/L per a non-aqueous solvent.

A non-aqueous solvent contained in the electrolyte solution includes in addition to the above ethyl methyl carbonate and ethylene carbonate, for example, propylene carbonate, γ-butyl lactone, dimethyl carbonate, and diethyl carbonate, etc. Further, non-aqueous solvents substituted by a halide such as a fluoro substituent or sulfur therein may be also used. Moreover, those non-aqueous solvents may be used alone or in a mixture of 2 or more solvents. Note when a mixture of 2 or more non-aqueous solvents is used, preferably used is a mixed solvent system, including a solvent with large viscosity such as a cyclic carbonate and a cyclic lactone together with a solvent with small viscosity such as a chain carbonate and a chain ester.

Hereinbefore, the electrolyte solution filled in the battery container 13 of the lithium secondary battery 1 has been described in detail. Herein, the electrolyte solution may contain an optional component other than the above described components in the range without deteriorating the advantageous effect of the present invention.

For example, preferably the electrolyte solution includes vinylene carbonate. Vinylene carbonate included in the electrolyte solution prevents a decomposition reaction of the electrolyte solution occurring at the surface of the negative electrode 12 (see FIG. 1). This enables cycle property of the lithium secondary battery 1 to be more improved. When vinylene carbonate is included in the electrolyte solution, preferably the concentration of vinylene carbonate in the electrolyte solution is set at 2 mass % or less.

Containing of vinylene carbonate provides the following effect. That is, although the details will be described later, the negative electrode 12 is made via applying a negative electrode mix including a negative electrode active material, etc. onto a collector and drying the mix, as described hereinafter. As a result, surface functional groups such as C=O, C—H and COO can exist on the surface of the negative electrode active material. Depending on a type of the surface functional groups, a surface film called an SEI film may be formed by the irreversible reaction between the surface functional groups and the electrolyte solution during a cell reaction.

Due to this, containing of vinylene carbonate in the electrolyte solution may contribute to the above reaction. This procedure suppresses the charge consumption in association with the formation of the SEI film, thereby to sufficiently prevent the battery capacity from deteriorating. In parallel with this, the SEM film suppresses the negative electrode 12 from reacting with the electrolyte solution at the interface therebetween with a temporal change, whereby a lithium secondary battery having an improved life (i.e., excellent in cycle property) may be provided.

Here, lithium hexafluorophosphate is used as an electrolyte as described above. However, in addition to lithium hexafluorophosphate, electrolytes of lithium salts such as $LiBF_4$, $LiClO_4$, $LiAsF_6$, $LiCF_3SO_2$, $Li(CF_3SO_2)_2N$, $Li(C_2F_5SO_2)N$, etc. may be used in combination. Note when electrolytes other than lithium hexafluorophosphate used in combination, preferably the total content of the included electrolytes other than lithium hexafluorophosphate may be set at less than 30 mass %.

Further, in addition to the above examples, a variety of compounds may be contained, including a compound having a carboxylic acid anhydride group, a compound having a sulfur element such as propane sultone, and an additive such as a compound containing boron for forming a film on a surface(s) of positive and/or negative electrode active material(s) to suppress a reductive decomposition of the electrode surface(s), an additive for suppressing overcharge such as biphenyl and cyclohexyl benzene. Moreover, included are an additive for providing the electrolyte solution with non-combustibility or non-flammability by substituting a phosphoric acid based group and/or halogen, an additive for suppressing elution of Mn from the positive electrode active material, an additive for improving the ionic conductivity of the electrolyte solution, a self-extinguishing additive, and an additive for improving wettability of the electrodes and the separator.

Those compounds may be contained appropriately in the electrolyte solution depending on a desirable object, as a single compound or a mixture of 2 or more compounds at an optional ratio. Note, for particularly exhibiting the specific effect of the present invention, preferably the total content of the additives thus contained may be set at less than 10 mass % in the electrolyte solution.

Next, again referring to FIG. 1, the overall structure of the lithium secondary battery 1 will be explained in detail. The lithium secondary battery 1 is an integrated product configured including a positive electrode 10, a separator 11, a negative electrode 12, a battery container 13, a positive electrode collector tab 14, a negative electrode collector tabs 15, an inner lid 16, an inner pressure release valve 17, a gasket 18, a positive temperature coefficient (PTC) resistor element 19, a battery lid 20, and an axial core 21. Further, the positive electrodes 10, the separator 11, and the negative electrode 12 are wound around the axial core 21.

The separator 11 is inserted between the positive electrode 10 and the negative electrode 12. In an electrode group formed by winding the positive electrodes 10, the separator 11 and the negative electrode 12 around the axial core 21, any optional axial core may be used as the axial core 21 so long as the axial core supports the positive electrode 10, the separator 11 and the negative electrode 12. In this embodiment, the electrode group is formed as a cylindrical shape. Further, the battery container 13 is formed as a cylindrical shape conforming to the shape of the electrode group.

A material of the battery container 13 is selected from an anticorrosive material to the electrolyte solution, for example, aluminum, stainless steel, nickel plated steel, etc. Herein, the selection of the material for the battery container 13 is conducted such that corrosion of the battery container 13 and deterioration of material caused via alloying with lithium ions do not occur to a portion in contact with the electrolyte solution when the battery container 13 is electrically connected with the positive electrode 10 or the negative electrode 12.

The electrode group is housed in the battery container 13. After the negative electrode collector tab 15 is connected to an inner wall of the battery container 13, the positive electrode collector tab 14 is connected to a bottom of the battery lid 20. The electrolyte solution (i.e., electrolyte solution for a lithium secondary battery, described hereinafter) is injected into an inside of the electric container 13 before sealing the battery. A method for injecting the electrolyte solution includes a method for directly adding the electrolyte solution to the electrode group while the battery lid 20 is opened, or a method for adding the electrolyte solution through an injection port arranged at the battery lid 20.

Then, the battery lid 20 is tightly fixed onto the battery container 13 to seal the entire battery. When an injection port of the electrolyte solution is provided, this port is also sealed. The battery may be sealed by using any technique such as welding or caulking.

<Positive Electrode 10>

The positive electrode 10 is configured including a positive electrode active material, a conductive agent, a binder and a collector. Specifically, the positive electrode is produced via mixing the positive electrode active material with the binder, the conduction agent and, carboxymethyl cellulose and a solvent, etc. where necessary to prepare slurry of a positive electrode mix. Here, NMP (N-methylpyrrolidone) may be used as a solvent.

Then, after coating the slurry of the positive electrode mix to the collector by a doctor blade method, a dipping method or a spray method, the positive electrode may be produced via drying the organic solvent, and conduction press formation by a roll press. Further, a plurality of mix layers may be stacked on the collector via repeating the steps of coating and drying the slurry of the positive electrode mix a plurality of times.

The positive electrode active material includes, for example, $LiCoO_2$, $LiNiO_2$, $LiMn_2O_4$, $LiMnO_3$, $LiMn_2O_3$, $LiMnO_2$, $Li_4Mn_5O_{12}$, $LiMn_{2-x}M_xO_2$ (where M is at least one member selected from the group consisting of Co, Ni, Fe, Cr, Zn and Ti, and x is 0.01 to 0.2), $Li_2Mn_3MO_8$ (where M is at least one member selected from the group consisting of Fe, Co, Ni, Cu and Zn), $Li_{1-x}A_xMn_2O_4$ (where A is at least one member selected from the group consisting of Mg, B, Al, Fe, Co, Ni, Cr, Zn and Ca, and x is 0.01 to 0.1), $LiNi_{1-x}M_xO_2$ (where M is at least one member selected from the group consisting of Co, Fe and Ga, and x is 0.01 to 0.2). Further, the positive electrode active material includes $LiFeO_2$, $Fe_2(SO_4)_3$, $LiCo_{1-x}M_xO_2$ (where M is at least one member selected from the group consisting of Ni, Fe and Mn, and x is 0.01 to 0.2), $LiNi_{1-x}M_xO_2$ (where M is at least one member selected from the group consisting of Mn, Fe, Co, Al, Ga, Ca and Mg, and x is 0.01 to 0.2), $Fe(MoO_4)_3$, $FeF_3$, $LiFePO_4$ and $LiMnPO_4$.

A particle size of the positive electrode active material is usually defined to be equal to or less than the thickness of a mix layer formed by the positive electrode active material, the conductive agent and the binder. When coarse particles having a size equal to or more than a thickness of the mix layer are included in the powder of the positive electrode active material, it is preferable to remove the coarse particles in advance by separation with a sieve or wind stream, etc. to prepare particles having a size equal to or less than the thickness of the mix layer.

Further, the positive electrode active material is an oxide type compound, which generally provides the material with high electric resistance. Therefore, preferably a conductive agent including a carbon powder, etc. may7 be used for compensating the electric conductivity. Moreover, both of the positive electrode active material and the conductive agent are usually powders. Thus, a binder may be mixed to the powders allowing the powders to be bonded each other and adhered to the collector.

As a collector of the positive electrode 10, used are, for example, an aluminum foil with the thickness of 10 μm to 100 μm, a punctured aluminum foil having a thickness of 10 μm to 100 μm and a pore diameter of 0.1 mm to 10 mm, an expanded metal or foamed metal plate, etc. Further, in addition to aluminum, materials such as stainless steel and titanium may also be used. Herein, any collectors may be used without specifically limiting a material, a shape, a production method, etc of the collectors.

When both surfaces of the collector are coated with the positive electrode mix, preferably a thickness of the mix layer on each surface may be about 50 μm to 200 μm. However, the thickness thereof is not limited to the above range.

As a binder used for the positive electrode 10, polyvinylidene fluoride (PVDF), an acryl polymer, a polymer having an imide group or an amide group, etc. may be used. Here, an excess amount of the binder used in the positive electrode mix layer may increase the internal resistance value and deteriorate the battery capacity. On the other hand, if an insufficient amount of the binder used may lower the adhesion strength of the electrode, leading to difficulty in the production of the electrode or deterioration of the storage property and the cycle property of the battery.

Accordingly, preferably the amount of the binder is appropriately determined while considering the balance among the above features. Specifically, the amount of the binder is preferably set at 1 mass %-7 mass % per the total amount of the positive electrode active material, the conductive agent and the binder. A desirable mixing ratio is preferably determined based on the results in tests of storage property and cycle property, etc. of the battery.

<Separator 11>

The separator 11 is used for preventing a short circuit from causing via direct contact between the positive electrode 10 and the negative electrode 12. Herein, a microporous polymer film made of polyethylene, polypropylene, aramid resin, etc. or a membrane formed via covering a thermo resistant material such as aluminum particles on a surface of a polymer film may be applied to the separator 11.

<Negative Electrode 12>

The negative electrode is configured including a negative electrode active material, a binder and a collector. Specifically, the negative electrode active material is mixed into the binder such as a styrene butadiene co-polymer and where necessary carboxymethylcellulose and a solvent, etc. to prepare slurry of a negative electrode mix. As a solvent, for example, the same solvent as in the production of the positive electrode 10 may be used. Then, after coating the slurry of the negative electrode mix to the collector by a doctor blade method, a dipping method or a spray method, the negative electrode may be produced via drying the organic solvent, and conducting press formation by a roll press. Further, a plurality of mix layers may be stacked on the collector via repeating the steps of coating and drying the slurry of the negative electrode mix a plurality of times.

A negative electrode active material to be used includes, for example, an easily graphitizable material obtained from natural graphite, petroleum coke, or coal pitch coke treated at a high temperature of 2,500° C. or more, mesophase carbon, amorphous carbon, graphite coated at a surface thereof with amorphous carbon, a carbon material in which crystallinity of a surface thereof is lowered by mechanically treating a surface of natural or artificial graphite, a material formed by coating and adsorbing an organic material such as a polymer on a carbon surface, a carbon fiber, metal lithium, a metal alloyed with lithium, a material including a metal supported on surfaces of carbon particles.

A metal to be supported includes, for example, a metal selected from lithium, aluminum, tin, silicon, indium, gallium and magnesium or alloys thereof. Further, an oxide of a metal such as tin, silicon, iron, and titanium may also be used as the negative electrode active material. Such a negative electrode active material may be used alone or as a mixture of two or more members.

A particle size of the negative electrode active material is usually defined to be equal to or less than a thickness of a mix layer formed by the negative electrode active material and the binder. When coarse particles having a size more than the thickness of the mix layer are included in the powder of the negative electrode active material, it is preferable to remove the coarse particles in advance by separation with a sieve or wind stream, etc. to prepare particles having a size equal to or less than the thickness of the mix layer.

A copper foil, etc. may be used for the collector of the negative electrode 12. For example, preferably a copper foil, etc. with a thickness of about 7 µm-25 µm is used. Further, when both surfaces of the collector are coated with the negative electrode mix, preferably the thickness of the mix layer on each surface is set at about 50 µm-200 µm. However, the thickness thereof is not limited to the above range.

A binder to be used includes a polymer which is dissolved, swollen or dispersed in water. For example, preferably used are a styrene-butadiene rubber co-polymer, a polymer having an acrylic group, and a polymer having a cyano group, etc. The amount of the binder in the negative electrode mix layer is preferably set at about 0.8 mass %-1.5 mass % based on the total amount of the negative electrode active material, carboxymethyl cellulose, etc. that is used for improving the thickening effect, and the binder. Herein, when the amount of the binder is excessively large, this increases the internal resistance value and lowers the battery capacity. On the other hand, when the amount of the binder is insufficient, this lowers adhesion strength of the electrode, leading to difficulty in the battery production and deterioration of storage property and cycle property of the battery.

Here, it should be noted that the organic material per se such as carboxymethyl cellulose which is added for improving the thickening effect of slurry of the mix may sometimes exert an effect of improving the binding force. Further, a preferable amount of the binder thus used may greatly vary depending on the active material to be used. Therefore, the mixing ratio of the binder is preferably determined based on the results in tests on the initial property, storage property and cycle property, etc. of the battery.

Meanwhile, an organic binder which is not dissolved, swollen, or dispersed in water may also be used. When the organic binder is used, an amount thereof, for example, may be set at about 3 mass %-6 mass % based on the total amount of the negative electrode active material, carboxymethyl cellulose and the binder. A desirable mixing ratio of the binder is preferably determined based on the results in tests of storage property and cycle property, etc. of the battery, similarly to the determination of the aqueous binder.

Hereinbefore, the entire structure of the lithium secondary battery 1 shown in FIG. 1 has been described. However, the shape of the lithium secondary battery 1 is not limited to the shape illustrated in FIG. 1. For example, in the embodiment of FIG. 1, the electrode group is formed as a cylindrical shape. However, various shapes may be applicable thereto, for example, including an electrode group formed via stacking strip-like electrodes, and an electrode group formed via winding the positive electrode 10 and the negative electrode 12 into an optional shape such as a flat shape.

A shape of the battery container 13 may be, for example, a flat oval shape, a flat elliptic shape, or a square shape in addition to the cylindrical shape described above. Further, the axial core 21 may be omitted depending on the shape of the battery or in order to improve a volume occupancy ratio of the electrode inside the battery.

Further, the present invention is not limited to the embodiments described hereinbefore, and various modifications are included therein. For example, a part of the components defined in any embodiment may be deleted, added with, or replaced by any component defined in other embodiments.

EXAMPLES

A series of lithium secondary batteries 1 illustrated in FIG. 1 were produced by the following method. The respective lithium secondary batteries 1 thus produced were evaluated in the cycle property thereof.

Example 1

A lithium secondary battery 1 illustrated in FIG. 1 was produced by using an electrolyte solution containing $(O-CH_2CH_2CH_2CH_3)_3(BO)_3$ as a boroxine compound (1), and then cycle property of the lithium secondary battery 1 was evaluated. Here, $(O-CH_2CH_2CH_2CH_3)_3(BO)_3$ is a boroxine compound (1) liquefying at 25° C. and includes liner alkyl groups each having 4 carbon atoms.

Note, in the descriptions below, a boroxine compound (1) represented by the chemical formula of $(O-CH_2CH_2CH_2CH_3)_3(BO)_3$ may be called a "boroxine compound (A)" for convenience of explanation.

<Preparation of Boroxine Compound (A)>

The boroxine compound (A) was prepared in the following method. Under Ar atmosphere, $(O-CH_2CH_2CH_2CH_3)_3$ (10 g, 0.043 mol) and $B_2O_3$ (3.0 g, 0.043 mol) were mixed at equivalent molar amounts to undergo a cyclization reaction. As a result, the boroxine compound (A) was obtained in 99% yield (12.8 g). Note, $(O-CH_2CH_2CH_2CH_3)_3$ was sufficiently dehydrated, and distilled to be a highly pure material before used in the reaction.

<Preparation of Electrolyte Solution>

Lithium hexafluorophosphate was dissolved as an electrolyte at a concentration of 1 mol/L into a mixed solution of ethylene carbonate (EC) and ethyl methyl carbonate (EMC) (EC:EMC=1:2 (volume ratio)) serving as a non-aqueous solvent. Then, the boroxine compound (A) was dissolved in the mixed solution such that the concentration thereof became 0.5 mass % per the total amount of lithium hexafluorophosphate and the non-aqueous solvent.

<Preparation of Negative Electrode 12>

Natural graphite having a spacing of 0.368 nm analyzed by X-ray diffractometry, an average particle size of 20 μm and a specific surface area of 5 $m^2/g$ was used as the negative electrode active material. An aqueous liquid dispersion containing the natural graphite, water swollen carboxymethyl cellulose, and a styrene-butadiene copolymer was sufficiently kneaded by using a mixer having a stirring device such as a rotary blade, to prepare slurry of a negative electrode mix. The mixing ratio of the negative electrode active material, carboxymethyl cellulose, and the styrene-butadiene copolymer was 97:1.5:1.5 by mass.

The slurry of the native electrode mix was coated substantially uniformly on both surfaces of the rolled copper foil with 10 μm thickness (i.e., collector). After drying, the product underwent compression molding such that the density of the active material of the negative electrode 12 became about 1.5 $g/cm^3$ by a roll press to produce a negative electrode. After pressing for density control, the product was cut so as to have a 55 cm coating length of the mix layer and a 5 cm uncoated area, that is, to have the total length of 60 cm and the coating width of 5.6 cm. Then, a Ni lead was welded to the uncoated area to produce a negative electrode 12 provided with a current lead-out portion.

<Preparation of Positive Electrode 10>

A positive electrode active material used was $Li_{1.02}Mn_{1.98}Al_{0.02}O_4$ having an average particle size of 10 μm and a specific surface area of 1.5 $m^2/g$. Slurry of a positive electrode mix was prepared via dispersing the positive electrode active material and a conductive agent formed by mixing the massive graphite and acetylene black at 9:2 ratio in an N-methylpyrrolidone (NMP) solution containing PVDF previously adjusted to 5 mass % as a binder.

The mixing ratio of the positive electrode active material, the conductive agent and PVDF was set at 85:10:5 by mass. Further, in preparation of the slurry, the mixture was sufficiently kneaded by using a mixer provided with a stirring device such as a rotary blade, similarly to the preparation of the negative electrode.

The slurry of the positive electrode mix was coated to both surfaces of an aluminum foil having a 20 μm thickness (i.e., collector) uniformly and homogeneously as much as possible and dried in the same procedure as in the negative electrode 12. Then, the product underwent compression molding by a roll press such that the density of the active material of the positive electrode 10 became 2.6 $g/cm^3$. Then, the resulting product was cut so as to have a 50 cm coating length of the mix layer and a 5 cm uncoated area, that is, to have a 55 cm length in total. After that, a lead of an aluminum foil for leading out current was welded to the uncoated area to produce a positive electrode 10 provided with a current lead-out portion.

<Assembly of Lithium Secondary Battery 1>

A cylindrical lithium secondary battery 1 as illustrated in FIG. 1 was produced by using the positive electrode 10, the negative electrode 12 and the electrolyte solution thus prepared as above. Specifically, a positive electrode collector tab 14 and a negative electrode collector tab 15 both for leading out current were supersonically welded to the positive electrode 10 and the negative electrode 12, respectively. The positive electrode collector tab 14 and the negative electrode collector tab 15 were respectively made of a metal foil of a material identical to that of the rectangular collector.

Further, a separator 11 formed as a single polyethylene layer film was put to be stacked between the positive electrode 10 and the negative electrode 12. Then, the separator 11, the positive electrode 10 and the negative electrode 12 were wound into a cylindrical shape (i.e., spiral shape) to form an electrode group, and housed in the battery container 13 with a cylindrical shape as illustrated in FIG. 1.

After housing the electrode group in the battery container 13, the electrolyte solution thus prepared was injected into the battery container 13. Then, a sealing battery lid 20 attached with the positive electrode collector tab 14 was tightly fixed via a gasket to the battery container 13, and sealed by caulking. Accordingly, through the above mentioned steps, a cylindrical lithium secondary battery 1 to with 18 mm in diameter and 650 mm in length was produced.

Example 2

A cylindrical lithium secondary battery 1 was produced in the same method as in Example 1 except for changing the content of the boroxine compound (A) included to the electrolyte solution to 1.0 mass %.

Example 3

A cylindrical lithium secondary battery 1 was produced in the same method as in Example 1 except for changing the content of the boroxine compound (A) included to the electrolyte solution to 2.0 mass %.

Example 4

A cylindrical lithium secondary battery 1 was produced in the same method as in Example 2 except for further containing vinylene carbonate in the electrolyte solution such that a concentration thereof became 2.0 mass %.

Example 5

A cylindrical lithium secondary battery 1 was produced in the same method as in Example 3 except for further containing vinylene carbonate in the electrolyte solution such that a concentration thereof became 2.0 mass %.

Example 6

A cylindrical lithium secondary battery 1 was produced in the same method as in Example 1 except for using a boroxine compound (B) represented by the chemical formula of (O—CH(CH$_3$)CH$_2$CH$_3$)$_3$(BO)$_3$ instead of the boroxine compound (A) defined as the boroxine compound (1). Herein, R of the boroxine compound (B) is a linear-chain alkyl group having 3 carbon atoms together with a branch having 1 carbon atom (i.e., having a branched methyl group). The boroxine compound (B) is also a compound liquefying at 25° C. the same as the boroxine compound (A).

Note the content of the boroxine compound (B) in the electrolyte solution is 0.5 mass % similarly to Example 1.

The boroxine compound (B) was prepared in the method the same as in Example 1 except for changing B(OCH$_2$CH$_2$CH$_3$)$_3$ used in Example 1 to B(OCH(CH$_3$)CH$_2$CH$_3$)$_3$. The boroxine compound (B) was obtained in 98% yield (12.6 g).

Example 7

A cylindrical lithium secondary battery 1 was produced in the same method as in Example 6 except for changing the content of the boroxine compound (B) included to the electrolyte solution to 1.0 mass %.

Example 8

A cylindrical lithium secondary battery 1 was produced in the same method as in Example 6 except for changing the content of the boroxine compound (B) included to the electrolyte solution to 2.0 mass %.

Example 9

A cylindrical lithium secondary battery 1 was produced in the same method as in Example 7 except for further containing vinylene carbonate in the electrolyte solution such that a concentration thereof became 2.0 mass %.

Example 10

A cylindrical lithium secondary battery 1 was produced in the same method as in Example 8 except for further containing vinylene carbonate in the electrolyte solution such that a concentration thereof became 2.0 mass %.

Comparative Example 1

A cylindrical lithium secondary battery 1 was produced in the same method as in Example 1 except for containing no boroxine compound (A) in the electrolyte solution.

Comparative Example 2

A cylindrical lithium secondary battery 1 was produced in the same method as in Example 3 except for using cyclohexoxyboroxine (where R is a cycloalkyl group in the formula (1)) that is a solid (i.e., powder) at 25° C. instead of boroxine compound (A). Note cyclohexiso boroxine had little solubility at 25° C. Thus, the compound was made to be dissolved in the electrolyte solution by heating the electrolyte solution at 50° C. for 4 hr.

Comparative Example 3

A cylindrical lithium secondary battery 1 was produced in the same method as in Comparative Example 2 except for using triphenylboroxine (where R is an aromatic ring in the formula (1)) that is a solid (i.e., powder) at 25° C. instead of cyclohexoxyboroxine.

Comparative Example 4

A cylindrical lithium secondary battery 1 was produced in the same method as in Example 3 except for using lithium tetrafluoroborate (LiBF$_4$) instead of lithium hexafluorophosphate (LiPF$_6$).

Comparative Example 5

A cylindrical lithium secondary battery 1 was produced in the same method as in Comparative Example 4 except for using cyclohexoxyboroxine that is a solid at 25° C. instead of boroxine compound (A).

[Evaluation of Cycle Property]

The respective lithium secondary batteries 1 produced in Examples 1-10 and Comparative Examples 1-5 as mentioned above were evaluated in a cycle load property test. Note in Comparative Example 3, the cycle load property test was not conducted due to insolubility of triphenylboroxine in the electrolyte solution.

First, the respective lithium secondary batteries 1 were put to constant-current/constant-voltage charge in a thermostatic bath at 25° C. at a charging current of 1500 mA and a voltage of 4.2 V for 3 hr. After an interval of 5 hr, constant-current discharge was performed at a discharging current of 1500 mA till the battery voltage was lowered to 3.0 V. Charge and discharge was performed for 3 cycles in total with the charge and discharge process being as one cycle.

A cycle load property test was performed with a discharge capacity at the third cycle being as 100%. The cycle load property test was repeated for 100 cycles, one cycle including constant-current and constant-voltage charge at a charging current of 1500 mA and a battery voltage of 4.2 V for 5 hr, leaving for 5 hr interval, and subsequent constant-current discharge at a discharging current of 1500 mA till lowering of the battery voltage was lowered to 3.0 V. After the test of 100 cycles, the ratio of the discharge capacity at a 100th cycle relative to the discharge capacity at the third cycle was determined. A larger ratio value means that the cycle property is more excellent.

[Results of Evaluation]

Results of the evaluation are listed in Table 1.

TABLE 1

| | Boroxine Compound | Electrolyte | Content of Boroxine Compound (mass %) | Content of Vinylene Carbonate (mass %) | Descharge Capacity After 100 cycles (%) | Solubility of Boroxine Compound |
|---|---|---|---|---|---|---|
| Example 1 | Boroxine Compound (A) | Li $PF_6$ | 0.5 | 0 | 84 | Easily Desolved (Liquid at 25° C.) |
| Example 2 | Boroxine Compound (A) | Li $PF_6$ | 1.0 | 0 | 87 | Easily Desolved (Liquid at 25° C.) |
| Example 3 | Boroxine Compound (A) | Li $PF_6$ | 2.0 | 0 | 87 | Easily Desolved (Liquid at 25° C.) |
| Example 4 | Boroxine Compound (A) | Li $PF_6$ | 1.0 | 2.0 | 92 | Easily Desolved (Liquid at 25° C.) |
| Example 5 | Boroxine Compound (A) | Li $PF_6$ | 2.0 | 2.0 | 94 | Easily Desolved (Liquid at 25° C.) |
| Example 6 | Boroxine Compound (B) | Li $PF_6$ | 0.5 | 0 | 85 | Easily Desolved (Liquid at 25° C.) |
| Example 7 | Boroxine Compound (B) | Li $PF_6$ | 1.0 | 0 | 87 | Easily Desolved (Liquid at 25° C.) |
| Example 8 | Boroxine Compound (B) | Li $PF_6$ | 2.0 | 0 | 91 | Easily Desolved (Liquid at 25° C.) |
| Example 9 | Boroxine Compound (B) | Li $PF_6$ | 1.0 | 2.0 | 94 | Easily Desolved (Liquid at 25° C.) |
| Example 10 | Boroxine Compound (B) | Li $PF_6$ | 2.0 | 2.0 | 94 | Easily Desolved (Liquid at 25° C.) |
| Comparative Example 1 | Not Included | Li $PF_6$ | 0 | 0 | 81 | Not Included |
| Comparative Example 2 | Cyclohexoxyboroxine | Li $PF_6$ | 2.0 | 0 | 82 | Desolved by Heating (Insoluble at 25° C.) |
| Comparative Example 3 | Triphenylboroxine | Li $PF_6$ | 2.0 | 0 | Not Tested | Insoluble; Evaluation Impossible |
| Comparative Example 4 | Boroxine Compound (A) | Li $BF_4$ | 2.0 | 0 | 69 | Easily Desolved (Liquid at 25° C.) |
| Comparative Example 5 | Cyclohexoxyboroxine | Li $BF_4$ | 2.0 | 0 | 68 | Desolved by Heating (Insoluble at 25° C.) |

In Example 1, the discharge capacity after 100 cycles was 84% of that at the third cycle, when the boroxine compound (1) was contained. In contrast, in Comparative Example 1, the discharge capacity after 100 cycles was 81% of that at the third cycle. As indicated above, the discharge capacity after 100 cycles was improved by incorporation of the boroxine compound (1) liquefying at 25° C., demonstrating good cycle property thereof. Therefore, according to the present invention, a lithium secondary battery 1 capable of preventing the aging deterioration and sufficiently improving the battery life is provided.

Further, as shown in Examples 2 and 3, the discharge capacities after 100 cycles were 87% respectively by incorporation of the boroxine compound (1) at 1.0 mass % to 2.0 mass %. The results indicated that the discharge capacity was improved by even 6 points compared to that in Comparative Example 1 containing no boroxine compound (1). Moreover, the results suggest that larger content of the boroxine compound (1) is more preferable when compared among Examples 1-3, while substantially the same effects are achieved when the content of the boroxine compound (1) reaches more than a certain level when compared between Examples 2 and 3.

Furthermore, it was found that the discharge capacity was further improved by incorporation of vinylene carbonate in addition to the boroxine compound (1). The discharge capacity in Example 5 containing the boroxine compound (1) at 2.0 mass % and vinylene carbonate at 2.0 mass % was remarkably improved by 13 points compared to that in Comparative Example 1 containing neither of the compounds. The results suggest that the reductive decomposition of the electrolyte solution on the surface of the negative electrode was suppressed by incorporation of vinylene carbonate. Therefore, it is assumed that a film formation reaction due to vinylene carbonate firstly proceeded, and this prevented decomposition of the boroxine compound and deterioration of the physical property of the electrolyte solution.

In Examples 1-5, the boroxine compound (A) was used as an example of the boroxine compound (1). Here, in Examples 6-10 using the boroxine compound (B) as another example of the boroxine compound (1), the same results were also shown as in Examples 1-5. Thus, it was found that good results were also obtained even when R in the boroxine compound (1) was changed.

On the other hand, in Comparative Example 2, although cyclohexoxyboroxine was dissolved in the electrolyte solution by heating, the discharge capacity in Comparative Example 2 (i.e., 82%) was substantially the same as in Comparative Example 1 (i.e., 81%) containing no boroxine compound. A reason therefor is assumed that decomposition of lithium hexafluorophosphate in the electrolyte solution is accelerated by heating. Additionally, triphenylboroxine used in Comparative Example 3 was not dissolved by heating, and the residues in the electrolyte solution were observed by looking.

Hereby, provided that triphenylboroxine was not dissolved and that decomposition of lithium hexafluorophosphate was accelerated by heating, it is assumed that the discharge capacities in both Comparative Examples may be lower than that in Comparative Example 1, although the cycle property thereof was not evaluated. Accordingly, those data indicate that it is preferable to use a boroxine compound (1) liquefying at 25° C. and dissolve the boroxine compound (1) in the electrolyte solution without heating excessively.

Further, in Comparative Example 4 using lithium tetrafluoroborate, the cycle property was remarkably lower than that in Example 3 using the same equivalent amount of the boroxine compound (A) as in Comparative Example 4 (i.e., 87% in Example 3 vs. 69% in Comparative Example 4). Additionally, the cycle property in Comparative Example 4 (i.e., 69%) was substantially the same as that in Comparative Example 5 (i.e., 69%) using cyclohexoxyboroxine which is a solid (i.e., powder) at 25° C.

Based on the above data, it was found that the excellent effect was achieved by using a boroxine compound (1) liquefying at 25° C. in combination with lithium hexafluorophosphate serving as an electrolyte.

What is claimed is:

1. A lithium secondary battery comprising:
   a positive electrode having a lithium-ion intercalation/deintercalation ability;

a negative electrode having a lithium-ion intercalation/de-intercalation ability; and a non-aqueous electrolyte solution contacted with the positive electrode and the negative electrode, wherein the non-aqueous electrolyte solution contains lithium hexafluorophosphate and a boroxine compound liquefying at 25° C. selected from the group consisting of $(O+CH_2CH_2CH_2CH_3)_3(BO)_3$ and $(O-CH(CH_3)CH_2CH_3)_3(BO)_3$.

2. The lithium secondary battery described in claim 1, wherein at least one of boron atoms of the boroxine compound is a tetravalent boron atom.

3. The lithium secondary battery described in claim 1, wherein a content of the boroxine compound is in the range from 0.1 mass % to 2 mass % defined as a concentration in the non-aqueous electrolyte solution.

4. The lithium secondary battery described in claim 1, wherein vinylene carbonate is further contained in the non-aqueous electrolyte solution.

5. An electrolyte solution for a lithium secondary battery, comprising
lithium hexafluorophosphate; and
a boroxine compound liquefying at 25° C. selected from the group consisting of $(O-CH_2CH_2CH_2CH_3)_3(BO)_3$ and $(O-CH(CH_3)CH_2CH_3)_3(BO)_3$.

6. The electrolyte solution for a lithium secondary battery described in claim 5, wherein at least one of boron atoms of the boroxine compound is a tetravalent boron atom.

7. The electrolyte solution for a lithium secondary battery described in claim 5, further comprising vinylene carbonate.

* * * * *